United States Patent
Mairet et al.

(10) Patent No.: US 10,711,232 B2
(45) Date of Patent: Jul. 14, 2020

(54) BIOREACTOR FOR MICROALGAE

(71) Applicants: Inria Institut National De Recherche En Informatique Et En Automatique, Le Chesnay (FR); Centre National De La Recherche Scientifique (C.N.R.S.), Paris (FR); Universite Pierre Et Marie Curie (Paris 6), Paris (FR)

(72) Inventors: Francis Mairet, Valbonne (FR); Olivier Bernard, Carros (FR); Antoine Sciandra, Villefranche sur Mer (FR); Eric Pruvost, Nice (FR); Charlotte Combe, Saint Laurent du Var (FR)

(73) Assignees: Inria Institut National De Recherche En Informatique Et En Automatique, Le Chesnay (FR); Centre National De La Recherche Scientifique (C.N.R.S.), Paris (FR); Universite Pierre Et Marie Curie (Paris 6), Paris (FR)

( * ) Notice: Subject to any disclaimer, the term of this patent is extended or adjusted under 35 U.S.C. 154(b) by 0 days.

(21) Appl. No.: 15/559,947

(22) PCT Filed: Mar. 18, 2016

(86) PCT No.: PCT/FR2016/050603
§ 371 (c)(1),
(2) Date: Jan. 4, 2018

(87) PCT Pub. No.: WO2016/151219
PCT Pub. Date: Sep. 29, 2016

(65) Prior Publication Data
US 2018/0112165 A1   Apr. 26, 2018

(30) Foreign Application Priority Data
Mar. 20, 2015 (FR) ..................... 15 52343

(51) Int. Cl.
*C12M 1/00* (2006.01)

(52) U.S. Cl.
CPC ............ *C12M 21/02* (2013.01); *C12M 23/22* (2013.01); *C12M 31/02* (2013.01); *C12M 41/06* (2013.01); *C12M 41/10* (2013.01)

(58) Field of Classification Search
CPC ...... C12M 21/02; C12M 23/22; C12M 31/02; C12M 41/06; C12M 41/10
USPC ........................................ 435/257.3
See application file for complete search history.

(56) References Cited

U.S. PATENT DOCUMENTS

| | | | |
|---|---|---|---|
| 2011/0312062 A1* | 12/2011 | Nordvik | C12M 21/02 435/257.1 |
| 2012/0156669 A1* | 6/2012 | Gonzalez | A01G 33/00 435/3 |
| 2012/0171733 A1 | 7/2012 | Im et al. | |

FOREIGN PATENT DOCUMENTS

| WO | 2008/033573 A2 | 3/2008 |
|---|---|---|
| WO | 2010/085853 A1 | 8/2010 |
| WO | 2011/080345 A2 | 7/2011 |

OTHER PUBLICATIONS

AlgaeBase, Scenedesmus obliquus (Turpin) Kutzing, Accessed Mar. 4, 2019, Available Online at: www.algaebase.org/ search/species/ detail/?species_id=27885.*
Bojan, Tamburic, et al., "Action Spectra of Oxygen Production and Chlorophyll a Fluorescence in the Green Microalga Nannochloropsis Oculata", Bioresource Technology, vol. 169, Jul. 8, 2014, pp. 320-327.

* cited by examiner

*Primary Examiner* — Jennifer M. H. Tichy
(74) *Attorney, Agent, or Firm* — Maynard, Cooper & Gale, P.C.; Brian Sattizahn (57) ABSTRACT

The invention relates to a bioreactor comprising a tank containing a culture medium in which a cell culture composed of algae cells is dispersed. The cell culture of algae has a concentration greater than 0.1 g/L in the culture medium, and each algal cell has a minimum absorption in a specific range of wavelengths of light. The bioreactor comprises a light source that is capable of emitting incident light in the direction of the tank, 60% of the photons of the incident light having a wavelength which is included in said specific range of wavelengths of light. The invention also relates to the use of the bioreactor for the production of biomass.

21 Claims, 8 Drawing Sheets

BIOREACTOR FOR MICROALGAE

The present invention relates to a bioreactor for producing microalgal biomass in a culture medium. The invention also relates to a process for producing microalgal biomass.

There are phototrophic prokaryotic and eukaryotic single-celled microorganisms, commonly collectively referred to as microalgae. Photosynthetic prokaryotic microorganisms are represented by cyanobacteria (sometimes referred to as "blue-green algae"). Photosynthetic eukaryotic microorganisms are diverse and are represented by a multitude of classes, among which mention may be made of chlorophyceae, diatoms, chrysophyceae, coccolithophyceae, euglenophyceae and rhodopyceae. In general, the size of a microalgal cell is between 1 μm and 100 μm.

It is currently estimated that there are more than one million species of microalgae, of which some tens of thousands of species are referenced. Microalgae are ubiquitous and are found both in freshwater and in brackish and sea waters.

The production of microalgae is an increasingly important sector. Indeed, microalgae synthesize numerous products of different natures, among which mention may be made of proteins, antioxidants, pigments, and the long-chain poly-unsaturated fatty acids DHA (docosahexaenoic acid) and EPA (eicosapentaenoic acid).

Thus, microalgae can be used in several technological fields, and especially in the cosmetics industry, the pharmaceutical industry, aquaculture, or the functional foods or dietary supplements industry.

Moreover, microalgae are used in the production of bioenergy. Indeed, microalgae have an ability to capture light energy, to fix and metabolize inorganic carbon from carbon dioxide ($CO_2$) in energetic molecules. Microalgae thus have significant purifying abilities. In addition, the coupling of microalgae with $CO_2$, and the fact that microalgae are often rich in sugars or oils, result in microalgae being of great interest in the production of biofuels.

Microalgae can be cultivated using natural light (sunlight) or artificial light. There are open culture systems of the culture pond type (also referred to as "raceway" pond) and closed culture systems of the photobioreactor type. In culture systems there is generally a tank filled with a culture medium. The microalgae are dispersed in the culture medium.

For a good production of microalgae under phototrophic conditions and independently of the culture system, nutrients (nitrogen, phosphorus, sulfur, trace elements, vitamins) and light must be provided for the microalgae. Indeed, in the presence of the necessary nutrients, microalgae can convert light energy by metabolizing $CO_2$ and thus produce oxygen and algal biomass (organic matter from microalgae). This is photosynthesis.

To obtain good productivity, it is therefore important to illuminate the microalgae. In general, light at a wavelength strongly absorbed by the microalgae is necessary in order to obtain a high growth rate. In practice, these are lights containing wavelengths in the blue and in the red.

The publications *Light requirements in microalgal photobioreactors: an overview of biophotonic aspects*—Carvalho et al., Appl Microbiology and Biotechnology, 2011, vol. 89, no. 5: 1275-1288 and *Light emitting diodes (LEDs) applied to microalgal production*—Schulze et al., Trends in Biotechnology, 2014, vol. 32, no. 8: 422-430, describe the use of light in systems for culturing microalgae.

In a bioreactor, the microalgal cells close to the light source (for example on the surface or at the periphery of the tank) receive an excess of photons. The excess photons absorbed by the microalgae leads to a decrease in photosynthetic efficiency. This is a dissipation of energy, referred to as non-photochemical quenching. The phenomenon of non-photochemical quenching is especially described in the publication *Non-Photochemical Quenching. A Response to Excess Light Energy*—Müller et al., Plant Physiol, 2001, vol. 125, no. 4: 1558-1566. Excess absorption of photons may also cause degradation of the photosynthetic machinery, a phenomenon referred to as photoinhibition.

In high-density cultures, that is to say with a high concentration of cells, the incident light is predominantly absorbed by the cells close to the light source. In other words, a large portion of the incident light fails to penetrate deep into the tank. A gradient of light is consequently created within the culture medium.

For these high-density cultures, a large amount of cells are located deep in the tank and therefore at a distance from the surface or the periphery. These deep cells may be located in the darkness, due to the fact that the light does not penetrate deep into the tank. The fixation of carbon by photosynthesis then no longer compensates for the energy losses by cellular respiration, based on the degradation of sugars that were synthesized during photosynthesis. It is therefore necessary to increase mixing in order to balance the distribution of light to the cells or to place light sources inside the tank.

In summary, high-density cultures present a problem of overexposure to light for the cells close to the light source and a problem of underexposure for the cells located deep in the culture medium.

Therefore, the solutions of the prior art propose culture systems with light sources with a high light intensity (preferably distributed around the periphery and/or inside the tank) combined with high-performance mixing tools. These systems are expensive in terms of energy.

There is also another approach, which consists in reducing the size of microalgal antennas. The reduction of antenna size is achieved by genetic modification of the microalgae. The aim of this approach is to make the microalgae more transparent. Each cell thus captures a lesser amount of light, which reduces the phenomenon of non-photochemical quenching. The cells located in the zones furthest away from the light source are therefore less shaded. However, this approach requires complex and costly genetic engineering methods.

The present invention improves the situation.

To this end, the invention aims to introduce a bioreactor comprising a light source and a tank comprising a culture medium in which a cell culture consisting of algal cells is dispersed, said algal cell culture having a concentration of greater than 0.1 g/l in the culture medium, each algal cell having a minimum absorption in a light-specific range of wavelengths, said source being capable of emitting incident light in the direction of the tank consisting of at least 60% of photons having a wavelength within the light-specific range of wavelengths.

Other advantages and characteristics of the invention will appear on reading the following detailed description and on the appended drawings, in which.

The following drawings and description essentially contain elements which are certain in nature. They are an integral part of the description and can thus not only serve to better elucidate the present invention, but also contribute to defining it, if necessary.

Figure 1:
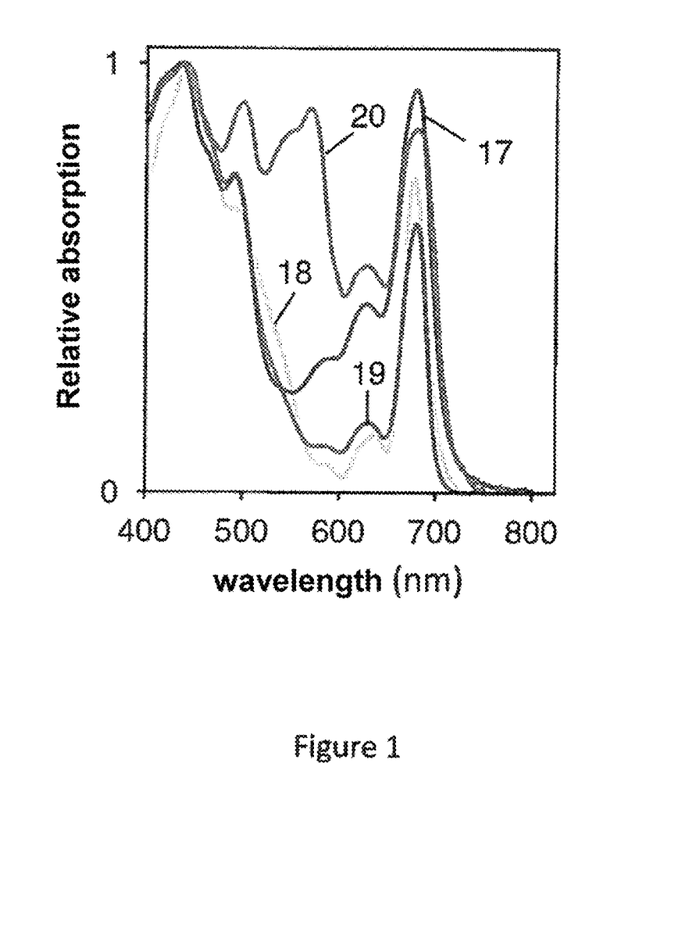
FIG. 1 shows a graph of absorption spectra of different microalgae.

FIG. 1 shows a graph of absorption spectra of different microalgae. This graph is taken from the publication *Colorful niches of phototrophic microorganisms shaped by vibrations of the water molecule*—Stomp et al., The ISME journal, Vol. 1, No. 4: 271-282, 2007.

Curve 17 shows the normalized absorption spectrum of a green alga *Chlamydomonas* sp. of the class Chlorophyceae; curve 18 shows the normalized absorption spectrum of *Phaeodactylum tricornutum* of the class Bacillariophyceae (or Diatomophyceae); curve 19 shows the normalized absorption spectrum of a Chrysophyceae *Isochrysis* sp. of the class Chrysophyceae; and curve 20 shows the normalized absorption spectrum of a red alga *Palmaria palmata* of the class Florideophyceae.

FIG. 1 shows that each type of microalga has a minimum absorption for light of a given wavelength. Indeed, the green alga 17, *Chlamydomonas* sp., has a minimum absorption of between 500 nm and 600 nm, the minimum absorption point is at approximately 550 nm; the alga of the class of the diatoms 18, *Phaeodactylum tricornutum*, has a minimum absorption of between 550 nm and 650 nm, the minimum absorption point is at approximately 600 nm; the alga of the chrysophyte class 19, *Isochrysis* sp., has a minimum absorption of between 550 nm and 650 nm, the minimum absorption point is at approximately 600 nm; the red alga 20, *Palmaria palmata*, has a minimum absorption of between 580 nm and 650 nm, the minimum absorption point is at approximately 600 nm.

These microalgae also have maximum absorption peaks. First peaks are observed for light of wavelengths between 430 nm and 470 nm (blue light) and second peaks are observed for light of wavelengths between 650 nm and 700 nm (red light).

According to the teachings of the prior art, in order to obtain a high production of biomass from a culture of microalgae, incident light L at a strongly absorbed wavelength would be used.

Figure 2:
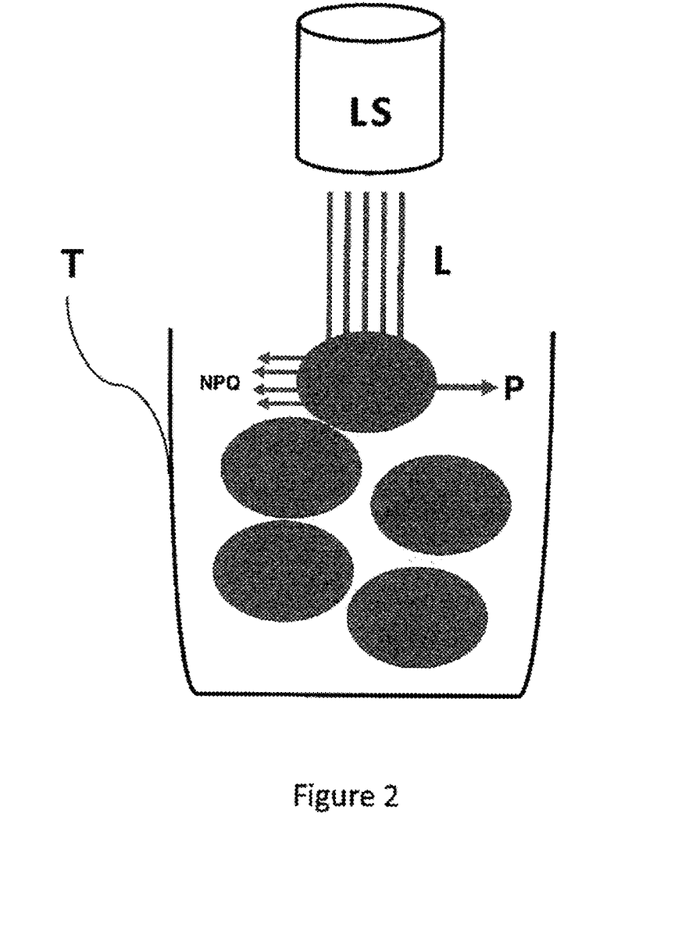
FIG. 2 shows a diagram of production of microalgal biomass in a culture system of the prior art.

FIG. 2 shows a diagram of production of microalgal biomass in culture systems of the prior art.

A light source LS emits an incident light L. The incident light L illuminates the microalgal cells located at the periphery of a bioreactor tank T. The incident light L provides photons to the microalgal cells located close to the light source (at the periphery).

The incident light is emitted at a wavelength that is strongly absorbed by the microalgal cells. The intensity of the incident light results in the phenomenon of non-photochemical quenching (NPQ), described above.

The microalgal cells located deep in the tank T are not illuminated and therefore do not receive photons.

Biomass production P is unsatisfactory.

Certain culture systems of the prior art use an improved mixing tool to thereby promote circulation of the microalgae within the tank. This at least partially enables the microalgal cells initially located within the tank to be exposed to incident light at the surface or at the periphery of the tank. The mixing of the cell culture results in a succession, on the microalgal cell scale, of illuminated and dark periods.

However, effective mixing of a culture medium represents a significant energy cost.

Moreover, in high-density cell cultures, mixing of the culture medium does not generally make it possible to completely avoid the deleterious effects caused by the light gradient (surface or peripheral photoinhibition and large amounts of respiration at depth).

The present invention proposes a radically different approach from that of the prior art. Furthermore, the present invention implements the opposite of the teachings and solutions proposed in the prior art. Indeed, the invention uses spectral lights with wavelengths which are weakly absorbed by the microalgae.

The Applicant has surprisingly discovered that the problems associated with the poor distribution of the photons within a high-density culture medium (light gradient) are greatly reduced by the use of light weakly absorbed by the microalgae. The overall photosynthetic efficiency of the culture system is thus increased.

While for low-density cultures this type of light causes slower growth, due to a low number of absorbed photons, for high-density cultures, this type of light promotes penetration of the photons into the culture medium. It follows that the use of light with a weakly absorbed wavelength enables better distribution of the light energy. Consequently, on the surface, dissipation losses and the effects of photoinhibition, which appear when a cell receives too many photons, are avoided. Light with a weakly absorbed wavelength therefore makes it possible to illuminate a larger volume of the culture medium than the lights used in the prior art.

Moreover, the cell cycle of microalgae is regulated, inter alia, by photoreceptors sensitive to blue and red light (see *Photoreceptors in algae*, Rudiger, W and Lopez-Figueroa, F, Photochemistry and Photobiology, Vol. 55, pp. 949-954, 1992). The absence of these wavelengths in the illumination has the effect of slowing the cell cycle (without, however, influencing photosynthesis), resulting in larger cells having a higher content of reserve carbon.

The invention thus makes it possible to improve the productivity of the system, reduce the necessary light energy and the associated costs, while reducing the energy required for harvesting the microalgal biomass.

What motivated the Applicant is that the quantum yield, that is to say the number of oxygen molecules synthesized per absorbed photon, is not very sensitive to the type of incident light. The quantum yield is thus virtually independent of the wavelength; this is described especially in the scientific publication *Action spectra of oxygen production and chlorophyll a fluorescence in the green microalga Nannochloropsis oculata*—Tamburic et al., Bioresource Technology vol. 169: 320-327, 2014.

Thus, in terms of metabolization, absorbed photons originating from light with a weakly absorbed wavelength have the same efficiency as absorbed photons originating from light with a strongly absorbed wavelength. This is especially described in the scientific publication *Aquatic photosynthesis*, Falkowski, P. G., & Raven, J. A., Princeton University Press, (2013).

For example, green photons, which are generally weakly absorbed by chlorophyte microalgae, have the same effect (once captured by cells) as red photons which are generally strongly absorbed by the microalgae. In short, once a photon is captured by a microalga, it will also be used for metabolism, regardless of its wavelength.

Figure 3:
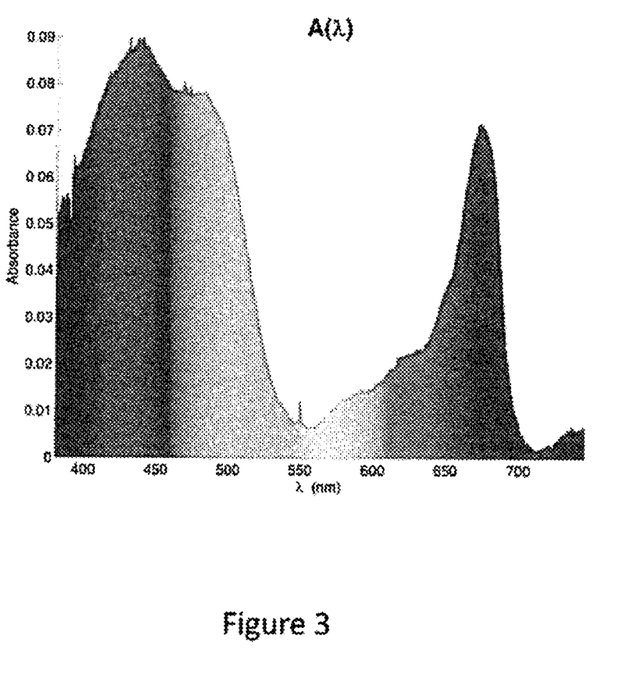
FIG. 3 shows a graph of the absorbance of a culture medium comprising microalgae, as a function of the wavelength of an incident light.

FIG. 3 illustrates the absorbance of a cell culture of Chlorophyceae *Dunalliela salina* as a function of the wavelength of an incident light. It can be seen from FIG. 3 that this type of green alga generally has little absorbance for wavelengths between 550 nm and 600 nm.

The phenomena of optics, absorbance and metabolization of photons in a bioreactor tank are detailed in *Microalgal biotechnology: potential and production*, C. Posten and C. Walter, de Gruyter, 2012 and *Handbook of Microalgal Culture: Applied Phycology and Biotechnology*, 2nd Edition, A. Richmond and Q. Hu, Wiley-Blackwell, 2013, to which the reader may refer.

In general, the optimization of biomass production is based on the cell growth of the microalgal culture. The concentration x (g/l) of microalgae in the culture medium changes as a function of the specific growth rate $\mu(x)$ (h$^{-1}$) (described below), the respiration rate r and the degree of dilution D of the culture medium.

Respiration corresponds to all the reactions that consume $O_2$ and carbon-based reserves (carbohydrates, lipids), and expel $CO_2$ to ensure cellular maintenance. Respiration is involved, especially, in the mechanisms of glycolysis, in the Krebs cycle, in the pentose phosphate pathway and in mitochondrial respiration.

The degree of dilution D is given by the flow rate (l/h) divided by the volume (l) of the culture medium. The flow rate is defined by the flow of liquid entering the bioreactor, which may differ from the output flow rate (the volume is then variable).

Thus, the cell growth x of the microalgal culture can be defined by the following formula I:

$$\dot{x} = (\mu(x) - r - D)x \quad \text{(I), in which}$$

$\dot{x}$ is the cell growth in the reactor;
$\mu(x)$ is the mean specific growth rate, which depends on the biomass due to self-shading;
r is the respiration rate;
D is the degree of dilution;
x is the concentration of microalgae in the culture.

To better determine the quality of the system, it is beneficial to measure the net biomass production P=Dx at equilibrium. Taking into account that at equilibrium $\dot{x}=0$, the following formula II is obtained, of the biomass production rate at equilibrium:

$$P = Dx = (\mu(x) - r)x \quad \text{(II), in which}$$

P is the biomass production rate;
D is the degree of dilution;
$\mu(x)$ is the specific growth rate;
x is the concentration of the algal cell culture;
r is the respiration rate.

The specific growth rate $\mu(x)$ corresponds to the mean growth of all the cells considered independently of one another, in a given volume L. The net growth rate of a cell is given by the difference between the carbon fixed by photosynthesis and the carbon lost by respiration.

Each cell must therefore be considered individually as a function of the light it receives. The metabolic activity of each cell must especially be considered. The metabolic activity of a cell corresponds to the state in which a cell is found, that is to say the balance between the photosynthetic activity thereof and the respiration activity thereof. The activity is dependent on the location of the cell in the culture medium. Indeed, depending on the location of the cell within the culture medium, the cell will receive a larger or smaller number of photons γ (detailed below). It follows that there is a local growth rate $\mu_z$ which is a function of the location z (or the depth z) in the bioreactor of height L. This local growth rate $\mu_z$ can be determined as a function of the number of photons absorbed according to the following formula III:

$$\mu_z = \varphi/\gamma(z,x)/\gamma(z,x) + k_1 + \gamma(z,x)^2/k_2 \quad \text{(III), in which}$$

$\mu_z$ is the local growth rate at a depth z;
γ is the number of photons absorbed by a cell;
$k_1$ is a saturation constant;
$k_2$ is an inhibition constant;
φ is a constant defining the maximum growth rate.

These constants $k_1$, $k_2$, and φ can be identified from measurements of the photosynthetic response as a function of light. By way of example, $k_1 = 7000$ µmol·s$^{-1}$·kg$^{-1}$, $k_2 = 284\,000$ µmol·s$^{-1}$·kg$^{-1}$ and φ=2 j$^{-1}$. These values give a maximum growth rate of 1.5 j$^{-1}$ corresponding to an intensity of 500 µmol·m$^{-2}$·s$^{-1}$.

The integral of the local growth rate $\mu_z$ of all the locations z over the entire depth L of the bioreactor provides the specific growth rate $\mu(x)$.

Thus, the specific growth rate can be determined by the following formula IV:

$$\mu(x) = 1/L \int_0^L \mu_z dz = \varphi/L \int_0^L \gamma(z,x)/\gamma(z,x) + k_1 + \gamma(z,x)^2/k_2 dz \quad \text{(IV), in which}$$

$\mu(x)$ is the mean specific growth rate;
$\mu_z$ is the local growth rate at a depth z;
γ is the number of photons absorbed by a cell;
$k_1$ is a saturation constant;
$k_2$ is an inhibition constant;
x is the concentration of the algal cell culture;
z is the location (or depth) of a cell;
φ is a constant defining the maximum growth rate;
L is the height of the bioreactor.

The number of photons γ captured by a cell is dependent on several parameters.

It is necessary to consider the intensity I of the light received by a cell. The intensity varies according to the wavelength λ, the concentration x of the microalgal culture and the location z of the cell. The intensity I can be qualified by the light attenuation due to the absorption and the diffusion of light by the other cells located closer to the light source (closer to the surface).

Indeed, in a cell culture, incident light is emitted with a certain intensity $I_{in}$ (what is referred to as "incoming intensity"). The light gradient within the bioreactor tank containing a high-density cell culture results in a variation in the light intensity within said tank. The intensity of the light output $I_{out}$ (what is referred to as "outgoing intensity") is attenuated relative to the intensity $I_{in}$.

Figure 4:
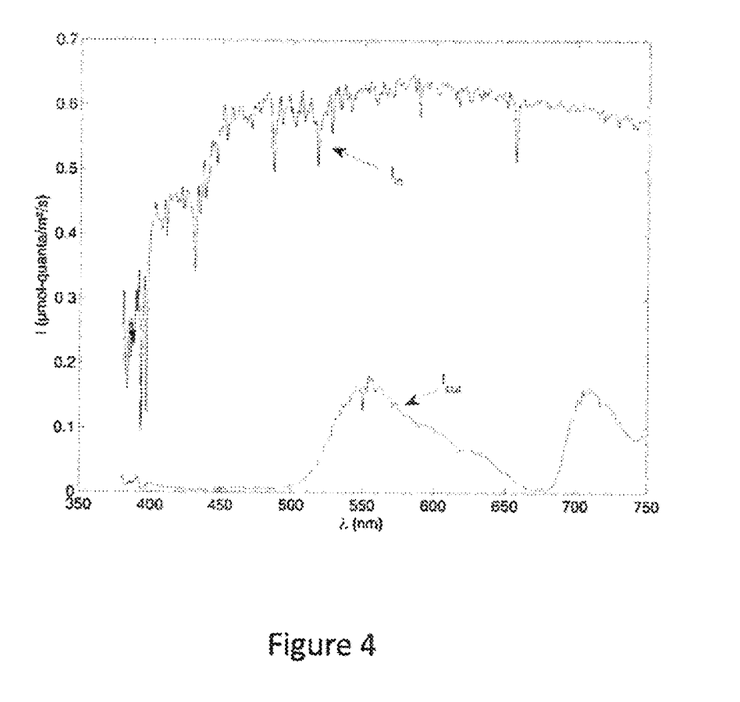
FIG. 4 shows a graph of the intensity of an incident light relative to the intensity of an outgoing light as a function of the wavelength.

FIG. 4 shows a graph of the intensity of the incident light $I_{in}$ and the intensity of the outgoing light $I_{out}$ as a function of the wavelength λ obtained for a culture of *Dunaliella salina* under natural light. A maximum outgoing light intensity is distinguished for wavelengths between 525 nm and 575 nm.

The intensity I of the light captured by a cell is therefore dependent on the intensity of the incident light $I_{in}$ of wavelength Δ but also on the attenuation profile (combination of absorption and diffusion) of the microalgal cell culture, on the concentration x and on the location z. For example, for a planar culture system, the intensity of light received locally at a depth z by a cell can be expressed by the following formula V:

$$I(\lambda,x,z)=I_{in}(\lambda)\exp(-K(\lambda)xz) \quad (V),$$ in which

I is the light intensity;
$I_{in}$ is the intensity of the incident light;
$\lambda$ is the wavelength;
K is the attenuation spectrum;
x is the concentration of the algal cell culture;
z is the location (or depth) of a cell.

Figure 5:
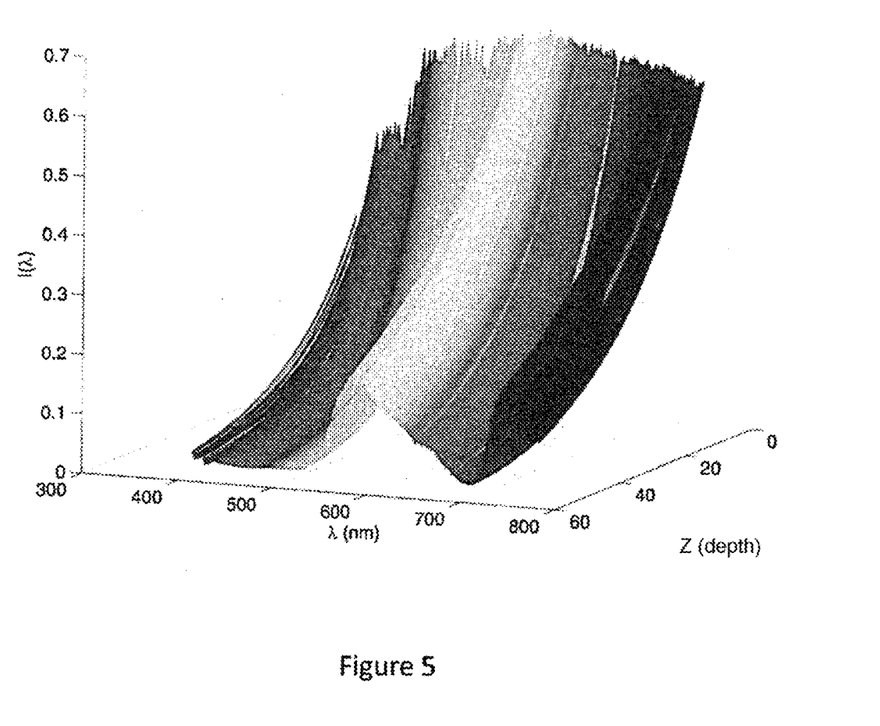
FIG. 5 shows a graph of light gradient in a microalgal culture medium.

FIG. 5 illustrates the light gradient in a planar bioreactor. Thus, FIG. 5 shows the intensity $I(\lambda)$ as a function of the wavelength $\lambda$ and as a function of the depth z of penetration in a culture medium.

In order to know the number of photons absorbed γ by a cell located at a depth z in a bioreactor tank containing a cell culture of concentration x, it is necessary to consider, over the set of wavelengths received by this cell, the intensity of the received light and the absorbance for said received wavelengths.

Thus, the number of photons absorbed is defined by the following formula VI:

$$\gamma(z,x)=\int_{\lambda_{min}}^{\lambda_{max}}I(\lambda,x,z)A(\lambda)d\lambda \quad (VI),$$ in which γ is the number of photons absorbed;
$\lambda_{min}$ is the minimum wavelength;
$\lambda_{max}$ is the maximum wavelength;
A is the absorption spectrum;
x is the concentration of the algal cell culture;
z is the location (or depth) of a cell.

Accordingly, when the intensity of the incident light, the absorption profile of the cells and their kinetic parameters are known, the production rate can be evaluated by means of formulas I to VI above.

From this observation, the Applicant carried out simulations of the productivity for incident lights of different wavelengths.

Figure 6:
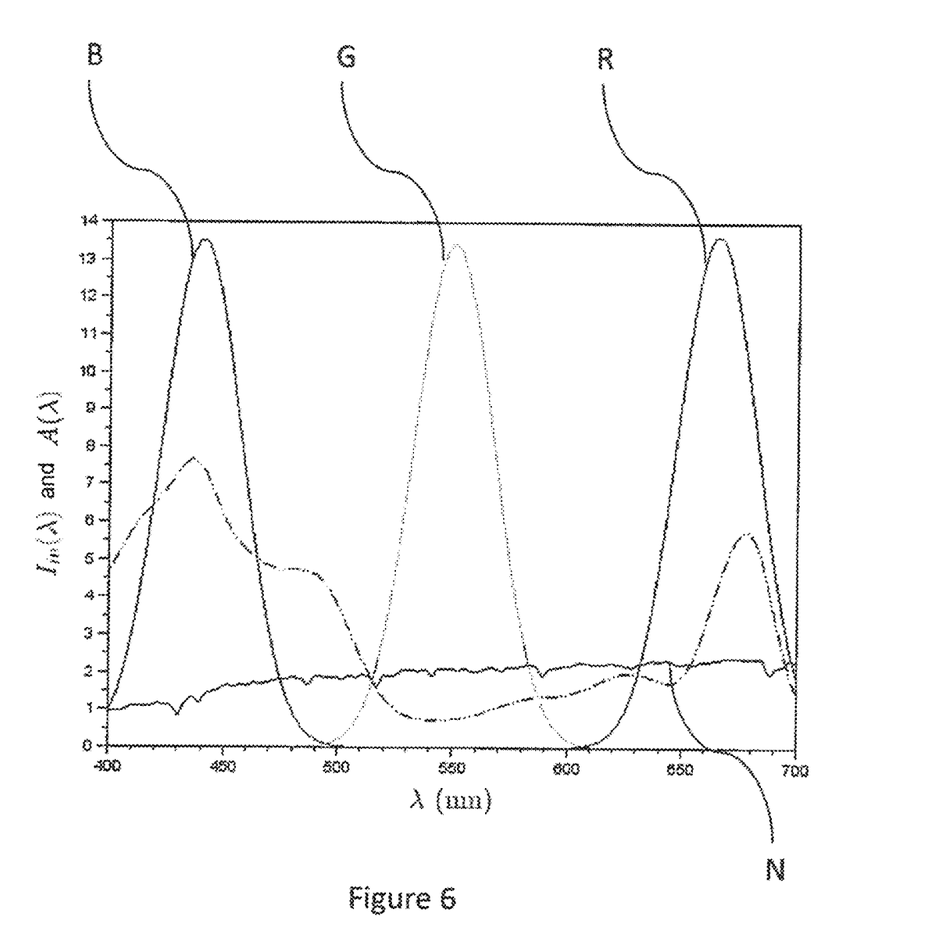
FIG. 6 shows simulations of the absorbance and of four different incident lights (having an equal number of photons) as a function of the wavelength.

FIG. 6 shows the absorbance $A(\lambda)$ of a microalga of the green algae type, and also four different spectra of incident lights $I_{in}(\lambda)$ (having an equal number of photons) as a function of the wavelength. The four lights are, respectively, natural light (N) (AM 1.5 spectrum of the *American Society for Testing and Materials*, representing the solar spectrum); blue light (B); green light (G); and red light (R).

The blue and red incident lights correspond to high absorption values, while the green light corresponds to a zone of low absorption.

Figure 7:
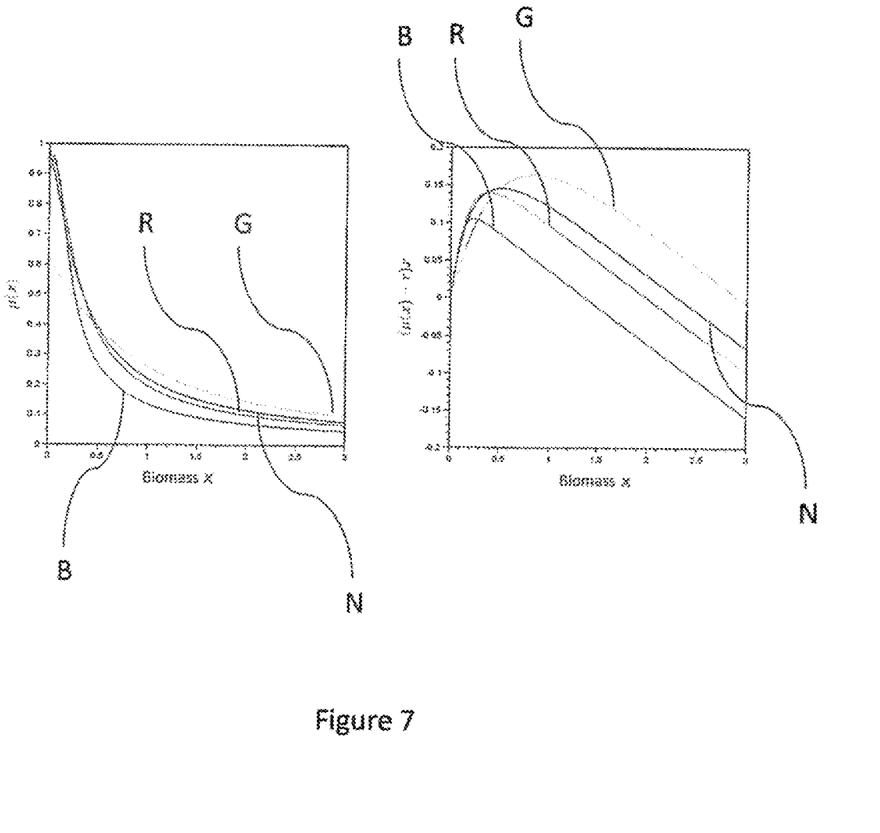
FIG. 7 shows the comparison between the specific growth rate and the net biomass production of an algal cell culture as a function of the concentration of biomass for different incident lights.

FIG. 7 shows the comparison, between the different lights, of the specific growth rate $[\mu(x)]$ of the biomass and the net productivity $[(\mu(x)-r)x]$ as a function of the cell concentration. At low cell density (concentration less than approximately 0.5 g/l) green light G gives a growth rate lower than natural light N, blue light B or red light R.

However, the Applicant has discovered, surprisingly, that at high cell density (concentration greater than approximately 0.5 g/l) green light gives a greater mean growth rate in the culture than natural light N, blue light B or red light R.

This motivated the Applicant to study lights having photons of particularly specific wavelength. Thus, favorable lights for increasing the mean growth rate in high-cell-density cultures were identified.

Most particularly, light in which more than 60% of the photons have a wavelength of between 500 nm and 650 nm, preferentially between 520 nm and 630 nm, more preferentially between 540 nm and 610 nm, and more preferentially still between 540 nm and 570 nm, is used in the present invention.

Figure 8:
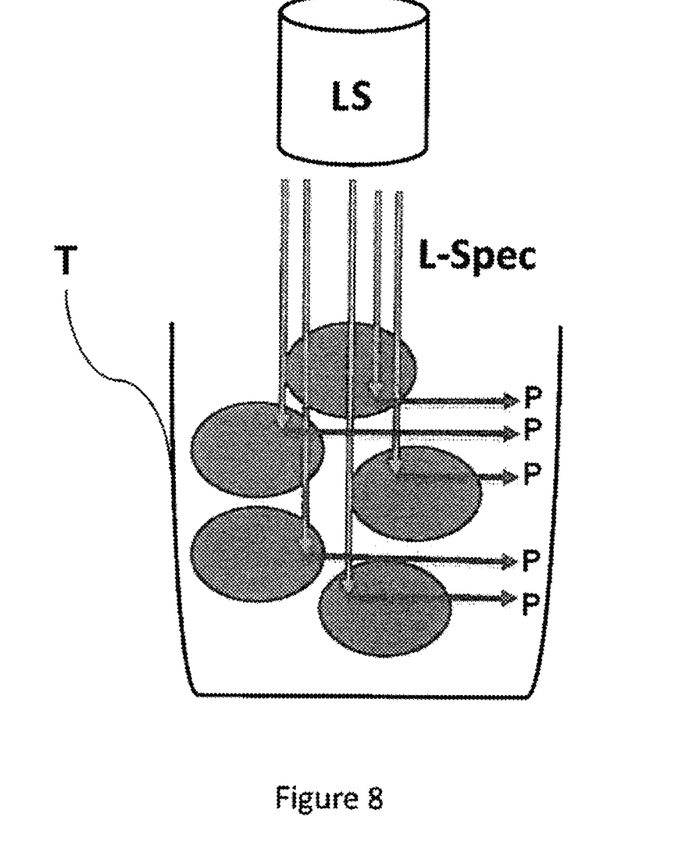
FIG. 8 shows a diagram of production of microalgal biomass in a bioreactor according to the invention.

FIG. 8 shows a diagram of production P of microalgal biomass in a bioreactor according to the invention. The use of an incident light L-spec, in which more than 60% of the photons have a wavelength of between 500 nm and 650 nm, preferentially between 520 nm and 630 nm, more preferentially between 540 nm and 610 nm, and more preferentially still between 540 nm and 570 nm, has several advantages:

The use of light with a wavelength within the ranges mentioned above makes it possible to limit the effects of non-photochemical quenching NPQ and photoinhibition.

Next, the weak absorption by the cells of the light employed according to the invention results in the photons not being completely absorbed by the cells on the surface. Photons can therefore penetrate deep into the culture medium in the tank T. In other words, a large part of the photons penetrates deeply and supplies energy to the cells located at depth. Photosynthesis is therefore substantially better distributed over all the microalgal cells.

The use of light with a wavelength within the ranges mentioned above avoids energy losses normally linked to the surplus of photons not metabolized by the algal cells.

The low proportion of blue and red light causes reduced activation of the photoreceptors coordinating the cell cycle, resulting in an increase in cell size and an increase in the reserve carbon content.

Finally, the best distribution of the photons enables a culture with a high cell concentration, which limits the energy requirements for stirring the culture, facilitates the harvesting of the microalgae and reduces water requirements. Thus, the invention makes it possible to work with cell cultures with a concentration greater than 0.1 g/l in open bioreactors. Open bioreactors comprise open-air ponds that generally have an oval course shape. These open bioreactors are commonly known by the name raceway-type bioreactors. The invention also makes it possible to work with cell cultures with a concentration greater than 0.5 g/l in closed bioreactors. In a particular embodiment, the concentration of the cell culture has a concentration of greater than 1 g/l.

The choice of the weakly absorbed spectral light L-Spec is a function of the species of microalgae cultivated. Indeed, it is the absorption spectrum of the species of microalgae that determines the selection of the spectral light. For example, for green algae (containing chlorophyll a and b), green light is weakly absorbed. A light spectrum of between 530 nm and 600 nm can be used. For a microalga containing no chlorophyll b (such as diatoms), a light spectrum between 530 nm and 650 nm may be used.

Thus, the bioreactor of the invention comprises a light source LS and a tank T. The tank comprises a culture medium in which a cell culture consisting of algal cells is dispersed. The algal cell culture has a concentration of greater than 0.1 g/l in the culture medium, and each algal cell has a minimum absorption in a light-specific range of wavelengths L-Spec. The light source LS is capable of emitting incident light in the direction of the tank T. This incident light consists of at least 60% of photons having a wavelength within the light-specific range of wavelengths L-Spec.

Each algal cell may especially have a minimum absorption in a light-specific range of wavelengths of between 500 nm and 650 nm, preferentially of between 520 nm and 630 nm, more preferentially between 540 nm and 600 nm, and even more preferentially between 540 nm and 570 nm. The incident light of the bioreactor then consists, respectively, of at least 60% of photons having a wavelength of between 500 nm and 650 nm, preferentially between 520 nm and 630 nm, more preferentially between 540 nm and 600 nm, and even more preferentially between 540 nm and 570 nm.

The light source may consist of one or more light-emitting diode (LED) panels. Each light-emitting diode panel then emits at least 60% of photons having a wavelength of between 500 nm and 650 nm, preferentially between 520 nm and 630 nm, more preferentially between 540 nm and 600 nm, and even more preferentially between 540 nm and 570 nm.

The light source may also be composed of sunlight coupled to at least one semi-transparent photovoltaic panel. Each semi-transparent photovoltaic panel is then arranged to filter sunlight and only allow passage of incident light consisting of at least 60% of photons having a wavelength of between 500 nm and 650 nm, preferentially between 520 nm and 630 nm, more preferentially between 540 nm and 600 nm, and even more preferentially between 540 nm and 570 nm.

The culture medium may also comprise an organic carbon source (mixotrophic culture).

The bioreactor may be driven by a supply mode selected from the group consisting of a batch supply mode, a fed-batch supply mode and a continuous supply mode.

According to one embodiment, the bioreactor is of the open (raceway) type.

According to another embodiment, the bioreactor is of the closed type. In this embodiment, the algal cell culture preferably has a concentration of greater than 0.5 g/l.

The algal cell culture may have a concentration of greater than 1.0 g/l.

In one embodiment, the light source may be of the LED type. This type of light source makes it possible to generate narrow light spectra, which makes it possible to target a precise range of wavelengths.

In another embodiment, the light source may be sunlight coupled to semi-transparent photovoltaic panels. In this mode, the panels allow, through optical filtration, passage of the range of the spectrum weakly absorbed by the microalgae. Advantageously, the spectral ranges absorbed by the panels are used for the production of photovoltaic electricity.

According to one embodiment, the bioreactor of the invention may be operated in semi-continuous or continuous mode (also referred to as a chemostat). In this embodiment, the bioreactor maintains a high density of cells in the culture medium in order to capture virtually all of the light. The high concentration of biomass also makes it possible to facilitate the harvesting operations, for example by centrifugation or filtration.

A procedure makes it possible to optimize the concentration of microalgae in the culture so as to maximize productivity.

The concentration of cells in the culture medium is a key parameter of biomass production. Too low a concentration results in a portion of the light energy not being captured by the cells. Too high a concentration results in respiration of the cells deep in the culture medium which is greater than the carbon fixation by photosynthesis. Either case negatively affects biomass productivity. The optimum concentration depends on the light source, the reactor geometry and the species cultivated. It is generally between 0.5 and 2 g/l.

In continuous operating mode and with a constant supply of light in a defined wavelength range, the biomass production process, in one embodiment of the invention, comprises the following steps:

1. Place a culture medium (for example of 5F type) in a photobioreactor (tubular, planar or columnar, etc.) or a culture pond,
2. Inoculate the culture medium with a selected microalgae species (e.g. *Chlorella vulgaris, Dunaliella salina, Haematococcus pluvialis, Arthrospira platensis*);
3. Operate the bioreactor in batch mode until a large biomass is obtained (concentration of the order of 1 g/l for example);
4. Operate with a constant degree of dilution $D_0$ until an equilibrium is reached (namely a constant biomass concentration), then measure the productivity obtained;
5. Set a variation factor of the degree of dilution p %, preferably 30%;
6. Operate with a new degree of dilution p % higher (or p % lower) until an equilibrium is reached;
7. Measure productivity at this equilibrium and:
    a. if the direction of variation of the degree of dilution and of the productivity are opposite, halve the variation factor of the degree of dilution p %.
    b. if productivity has increased, start step 6 again, increasing (or decreasing) the degree of dilution again;
    c. if productivity has decreased, start step 6 again, decreasing (or increasing) the degree of dilution.

Generally, the variation factor of the degree of dilution must be reset periodically or in the event of a disturbance.

The bioreactor may comprise a system for controlling the degree of dilution (a pump, the flow rate of which can be adjusted manually or controlled).

Changes in the degree of dilution can be adjusted as a function of disparities in productivity. If the disparity is large, the system is far from the optimum point of operation so the degree of dilution can be modified significantly. Conversely, if the productivity disparity between two degrees of dilution is low, the system is close to the optimum and small variations in the degree of dilution may be carried out. The degree of dilution will preferably be automatically adapted so that the loss of carbon by respiration in the dark areas of the reactor substantially compensates for the carbon fixation by photosynthesis.

The same steps can be carried out in an operating mode referred to as turbidostat: the degree of dilution is adjusted so as to set, to a reference value, the concentration of biomass (of the order of 0.5 to 2 g/l) or the light attenuation (between 90 and 99%). The choice of the setpoint (light attenuation or concentration of biomass) is adapted in order to optimize productivity, following the same adjustment procedure.

In operating modes of the day/night light type, the above steps can be used with the following modifications:
    The degree of dilution (or the setpoint, in turbidostat mode) is applied until a periodic regime is reached, namely the same cell concentration from one day to another at the same time;
    Productivity is calculated over a period, by integrating the instantaneous productivity over a period.

The productivity is evaluated by one or more sensors in the bioreactor, or manually.

The evaluation can be carried out at the reactor outlet (for example by measurements of flow rates and biomasses by dry weight, by optical density measurements, by cell counting, etc.). The productivity may also be evaluated by sensors arranged in the bioreactor to measure the liquid phase (oxygen sensor, carbon dioxide sensor, etc.) or the gaseous phase at the reactor outlet.

A relevant choice consists in regulating the pH in the culture medium by a controlled supply of $CO_2$ from a pH measurement. Regulating the pH ensures that the amount of dissolved $CO_2$ will be constant. It is then possible to evaluate the productivity of the system by the total amount of $CO_2$ injected over a certain period.

The bioreactor of the invention can therefore be operated in continuous mode. In this embodiment, the degree of dilution is adjusted manually or automatically so as to maximize the productivity estimated by oxygen production, $CO_2$ consumption or by measuring the in situ biomass (turbidity sensor) or after sampling (optical density, dry weight, etc.).

The process described above can be carried out in a bioreactor according to the invention. The invention therefore also targets the use of the bioreactor as defined above for the production of biomass from an algal cell culture. The algal cell culture is preferably selected from the group consisting of the Chlorophyceae classes, such as *Chlamydomonas* sp., *Dunaliella salina* and *Haematococcus pluvialis*, Bacillariophyceae (Diatomophyceae) such as *Phaeodactylum tricornutum* and *Odontella aurita*, Isochrysidaceae such as *Isochrysis galbana* and *Tisochrysis lutea*, Trebouxiophyceae such as *Chlorella vulgaris*, and Cyanophyceae such as *Arthrospira platensis*.

The invention claimed is:

1. A bioreactor comprising a light source and a tank comprising a culture medium in which a cell culture consisting of green algal cells is dispersed, said green algal cell culture having a concentration of greater than 0.1 g/l in the culture medium, each green algal cell having a minimum absorption for light in a range of wavelengths between 500 nm and 600 nm, said light source being configured to emit incident light in the direction of the tank consisting of at least 60% of photons having a wavelength between 500 nm and 600 nm.

2. The bioreactor as claimed in claim 1, wherein each green algal cell has a minimum absorption for light in a range of wavelengths of between 530 nm and 600 nm.

3. The bioreactor as claimed in claim 1, wherein the light source consists of at least one light-emitting diode panel, each light-emitting diode panel emitting at least 60% of photons having a wavelength of between 500 nm and 600 nm.

4. The bioreactor as claimed in claim 1, wherein the light source is composed of sunlight coupled to at least one semi-transparent photovoltaic panel, each semi-transparent photovoltaic panel being able to filter sunlight and only allow passage of incident light consisting of at least 60% of photons having a wavelength of between 500 nm and 600 nm.

5. The bioreactor as claimed in claim 1, wherein the culture medium comprises an organic carbon source.

6. The bioreactor as claimed in claim 1, wherein the bioreactor is driven by a supply mode selected from the group consisting of a batch supply mode, a fed-batch supply mode and a continuous supply mode.

7. The bioreactor as claimed in claim 1, the bioreactor being of an open type.

8. The bioreactor as claimed in claim 1, the bioreactor being of a closed type and the algal cell culture having a concentration of greater than 0.5 g/l.

9. The bioreactor as claimed in claim 1, wherein the algal cell culture has a concentration of greater than 1.0 g/l.

10. The bioreactor as claimed in claim 2, wherein each green algal cell has a minimum absorption in a light-specific range of wavelengths of between 540 nm and 570 nm.

11. The bioreactor as claimed in claim 3, wherein each light-emitting diode panel emitting at least 60% of photons having a wavelength of between 540 nm and 570 nm.

12. The bioreactor as claimed in claim 4, wherein each semi-transparent photovoltaic panel being able to filter sunlight and only allow passage of incident light consisting of at least 60% of photons having a wavelength of between 540 nm and 570 nm.

13. A bioreactor comprising a light source and a tank comprising a culture medium in which a cell culture consisting of red algal cells is dispersed, said red algal cell culture having a concentration of greater than 0.1 g/l in the culture medium, each red algal cell having a minimum absorption for light in a range of wavelengths between 580 nm and 650 nm, said light source being configured to emit incident light in the direction of the tank consisting of at least 60% of photons having a wavelength between 580 nm and 650 nm.

14. The bioreactor as claimed in claim 13, wherein the light source consists of at least one light-emitting diode panel, each light-emitting diode panel emitting at least 60% of photons having a wavelength of between 580 nm and 650 nm.

15. The bioreactor as claimed in claim 13, wherein the light source is composed of sunlight coupled to at least one semi-transparent photovoltaic panel, each semi-transparent photovoltaic panel being able to filter sunlight and only allow passage of incident light consisting of at least 60% of photons having a wavelength of between 580 nm and 650 nm.

16. A method for producing microalgal biomass comprising:
  dispersing a cell culture having algal cells in a tank comprising a culture medium, said algal cell culture having a concentration of greater than 0.1 g/l in the culture medium, each algal cell having a minimum absorption for light in a light-specific range of wavelengths such that the algal cell absorbs fewer photons from light having a wavelength within the light-specific range of wavelengths than from light having a wavelength outside of the light-specific range of wavelengths;
  selecting a light source based on said algal cell culture; and
  emitting, by the light source, incident light in the direction of the tank, wherein the incident light has at least 60% of photons having a wavelength within the light-specific range of wavelengths for said algal cell culture, and wherein the light-specific range of wavelengths for said algal cell culture is a range of wavelengths between 500 nm and 650 nm.

17. The method as claimed in claim 16, wherein said algal cell culture is a green algal cell culture and wherein the emitting incident light in the direction of the tank includes emitting incident light consisting of at least 60% of photons having a wavelength of between 500 nm and 600 nm.

18. The method as claimed in claim 16, further comprising producing biomass from said algal cell culture.

19. The method as claimed in claim 18, wherein the algal cell culture is selected from the group consisting of Chlorophyceae, Bacillariophyceae, Trebouxiophyceae, and Cyanophyceae.

20. The method as claimed in claim 16, wherein said algal cell culture is a red algal cell culture and wherein the emitting incident light in the direction of the tank includes emitting incident light consisting of at least 60% of photons having a wavelength of between 580 nm and 650 nm.

21. The method as claimed in claim 17, wherein the incident light consists of at least 60% of photons having a wavelength of between 540 nm and 570 nm.

* * * * *